US00PP33905P3

(12) United States Plant Patent
Schoone

(10) Patent No.: US PP33,905 P3
(45) Date of Patent: Jan. 25, 2022

(54) ***PHALAENOPSIS* PLANT NAMED 'GYPSY KISS'**

(50) Latin Name: *Phalaenopsis hybrida*
Varietal Denomination: Gypsy Kiss

(71) Applicant: FLORICULTURA B.V., Heemskerk (NL)

(72) Inventor: Rene Schoone, Assendelft (NL)

(73) Assignee: FLORICULTURA B.V., Heemskerk (NL)

( * ) Notice: Subject to any disclaimer, the term of this patent is extended or adjusted under 35 U.S.C. 154(b) by 0 days.

(21) Appl. No.: 17/339,972

(22) Filed: Jun. 5, 2021

(65) Prior Publication Data

US 2021/0385996 P1 Dec. 9, 2021

Related U.S. Application Data

(60) Provisional application No. 62/705,003, filed on Jun. 6, 2020.

(51) Int. Cl.
*A01H 5/02* (2018.01)
*A01H 6/62* (2018.01)

(52) U.S. Cl.
USPC ..... Plt./311

(58) Field of Classification Search
USPC ..... Plt./311
CPC ... A01H 5/02; A01H 5/00; A01H 5/08; A01H 6/62
See application file for complete search history.

*Primary Examiner* — June Hwu
(74) *Attorney, Agent, or Firm* — C. Anne Whealy

(57) ABSTRACT

A new and distinct cultivar of *Phalaenopsis* plant named 'Gypsy Kiss', characterized by its relatively compact and upright plant habit; moderately vigorous growth habit; strong flowering stems; strong leaves; freely flowering habit with typically two inflorescences per plant, each inflorescence with numerous flowers; large reddish purple-colored flowers with darker reddish purple-colored venation and very light purple-colored margins; and good postproduction longevity.

2 Drawing Sheets

Figure 1:
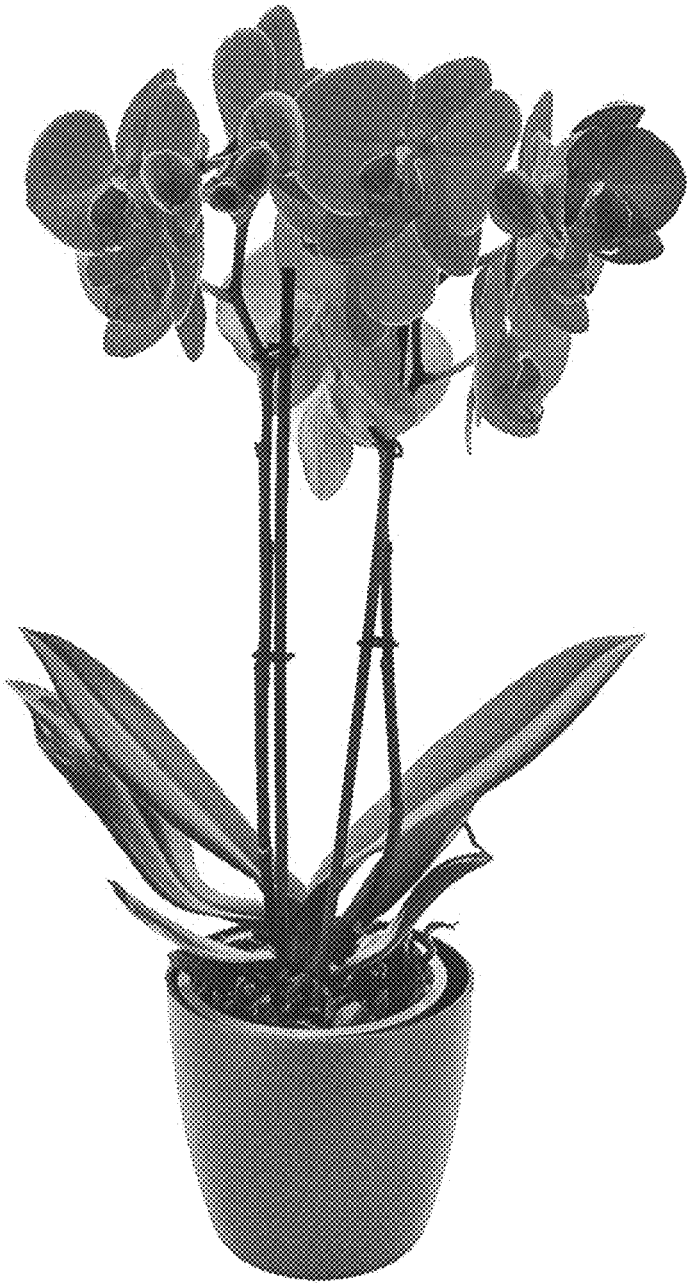

Botanical designation: *Phalaenopsis hybrida.*
Cultivar denomination: 'GYPSY KISS'.

STATEMENT REGARDING PRIOR DISCLOSURES BY INVENTOR AND APPLICANT/ASSIGNEE

An European Community Plant Breeder's Rights application for the instant plant was filed by the Applicant/Assignee of the instant application, Floricultura B.V. of Heemskerk, The Netherlands on Mar. 18, 2021, application number 2021/0831. Foreign priority is not claimed to this European Community Plant Breeder's Rights application.

The Inventor and Applicant/Assignee assert that no publications nor advertisements relating to sales, offers for sale or public distribution occurred more than one year prior to the effective filing date of this application. Any information about the claimed plant would have been obtained from a direct or indirect disclosure from the Inventor and/or Applicant/Assignee. Inventor and Applicant/Assignee claim a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Phalaenopsis* plant, botanically known as *Phalaenopsis hybrida*, and hereinafter referred to by the name 'Gypsy Kiss'.

The new *Phalaenopsis* plant is a product of a planned breeding program conducted by the Inventor in Den Hoorn and Heemskerk, The Netherlands. The objective of the breeding program is to develop new fast-growing and freely flowering *Phalaenopsis* plants with good leaf shape and large flowers with unique and attractive patterns and coloration.

The new *Phalaenopsis* plant originated from a cross-pollination in November, 2011 in Den Hoorn, The Netherlands of a proprietary selection of *Phalaenopsis hybrida* identified as code number ST 3708, not patented, as the female, or seed, parent with a proprietary selection of *Phalaenopsis hybrida* identified as code number ST 3676, not patented, as the male, or pollen, parent. The new *Phalaenopsis* plant was discovered and selected by the Inventor as a single flowering plant from within the progeny of the stated cross-pollination grown in a controlled greenhouse environment in Heemskerk, The Netherlands in January, 2018.

Asexual reproduction of the new *Phalaenopsis* plant by in vitro meristem propagation in a controlled environment in Assendelft, The Netherlands since January, 2019 has shown that the unique features of this new *Phalaenopsis* plant are stable and reproduced true to type in successive generations.

SUMMARY OF THE INVENTION

Plants of the new *Phalaenopsis* have been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Gypsy Kiss'. These characteristics in combination distinguish 'Gypsy Kiss' as a new and distinct *Phalaenopsis* plant:

1. Relatively compact and upright plant habit.
2. Moderately vigorous growth habit.
3. Strong flowering stems.
4. Strong leaves.
5. Freely flowering habit with typically two inflorescences per plant, each inflorescence with numerous flowers.
6. Large reddish purple-colored flowers with darker reddish purple-colored venation and very light purple-colored margins.
7. Good postproduction longevity.

Plants of the new *Phalaenopsis* can be compared to plants of the female parent selection. Plants of the new *Phalaenopsis* differ primarily from plants of the female parent selection in plant habit as plants of the new *Phalaenopsis* are shorter than plants of the female parent selection. In addition, flowers of plants of the new *Phalaenopsis* are reddish purple in color whereas flowers of plants of the female parent selection are purple in color.

Plants of the new *Phalaenopsis* can be compared to plants of the male parent selection. Plants of the new *Phalaenopsis* differ primarily from plants of the male parent selection in plant habit as plants of the new *Phalaenopsis* are shorter than plants of the male parent selection. In addition, flowers of plants of the new *Phalaenopsis* are reddish purple in color whereas flowers of plants of the male parent selection are violet in color.

Plants of the new *Phalaenopsis* can be compared to plants of *Phalaenopsis hybrida* 'Vivaldi', not patented. In side-by-side comparisons, plants of the new *Phalaenopsis* differ primarily from plants of 'Vivaldi' in flower color as plants of the new *Phalaenopsis* have flowers with very light purple-colored margin edges whereas plants of 'Vivaldi' have flowers that do not have very light purple or whitish-colored margin edges. In addition, the curvature of the labellum is stronger in plants of the new *Phalaenopsis* than plants of 'Vivaldi'.

BRIEF DESCRIPTION OF THE PHOTOGRAPHS

The accompanying photographs illustrate the overall appearance of the new *Phalaenopsis* plant showing the colors as true as it is reasonably possible to obtain in colored reproductions of this type. Colors in the photographs may differ slightly from the color values cited in the detailed botanical description which accurately describe the colors of the new *Phalaenopsis* plant.

The photograph on the first sheet (FIG. 1) is a side perspective view of a typical flowering plant of 'Gypsy Kiss' grown in a container.

Figure 2:
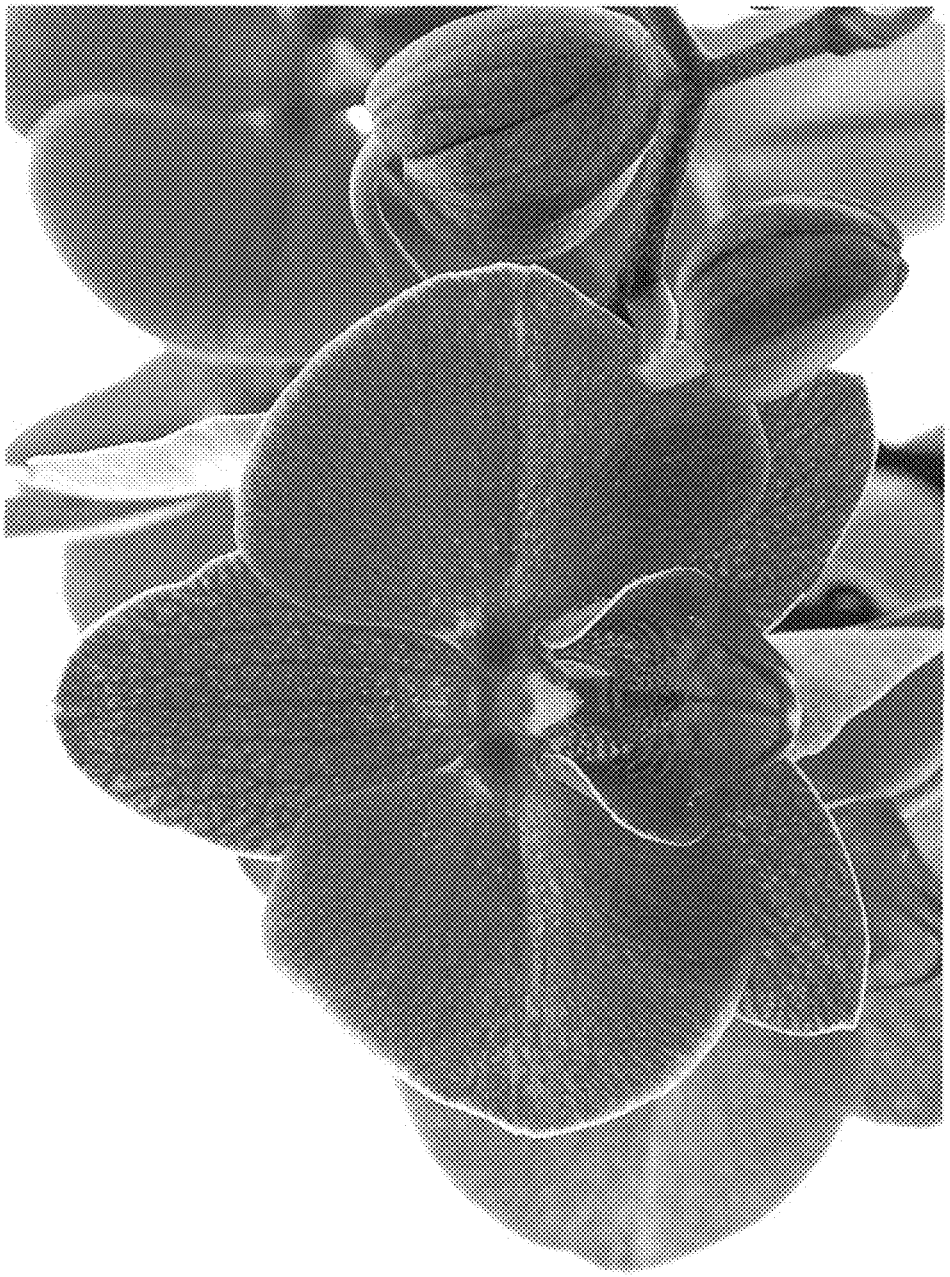

The photograph on the second sheet (FIG. 2) is a close-up view of a typical flower and flower buds of 'Gypsy Kiss'.

DETAILED BOTANICAL DESCRIPTION

The aforementioned photographs and following observations and measurements describe plants grown during the early spring in 10.5-cm containers in a glass-covered greenhouse in Heemskerk, The Netherlands and under cultural practices typically used in commercial *Phalaenopsis* production. Plants were 18 months old when the photographs and description were taken. During the first twelve months of production of the plants, day and night temperatures averaged 27° C. During the final six months of production of the plants, day temperatures ranged from 20° C. to 22° C. and night temperatures ranged from 18° C. to 20° C. During the 18 months of production, light levels ranged from a minimum of 5,000 lux to a maximum of 10,000 lux. In the following description, color references are made to The Royal Horticultural Society Colour Chart, 2015 Edition, except where general terms of ordinary dictionary significance are used.

Botanical classification: *Phalaenopsis hybrida* 'Gypsy Kiss'.

Parentage:

*Female parent.*—Proprietary selection of *Phalaenopsis hybrida* identified as code number ST 3708, not patented.

*Male parent.*—Proprietary selection of *Phalaenopsis hybrida* identified as code number ST 3676, not patented.

Propagation:

*Type.*—By in vitro meristem propagation.

*Time to initiate roots, summer and winter.*—About two weeks at temperatures about 28° C. to 30° C.

*Time to produce a rooted young plant, summer and winter.*—About 20 to 25 weeks at temperatures about 28° C. to 30° C.

*Root description.*—Thick, fibrous; typically grey to green in color; actual color of the roots is dependent on substrate composition, water quality, fertilizer, substrate temperature and age of roots.

*Rooting habit.*—Low amount of branching; medium density.

Plant description:

*Plant form and growth habit.*—Herbaceous epiphyte; relatively compact and upright plant habit with typically two inflorescences per plant, each inflorescence with numerous flowers; monopodial; moderately vigorous growth habit and moderate growth rate.

*Plant height, substrate level to top of foliar plane.*—About 13.5 cm.

*Plant height, substrate level to top of inflorescences.*—About 37.8 cm.

*Plant diameter or spread.*—About 27.5 cm.

Leaf description:

*Arrangement and quantity.*—Distichous, simple; sessile; about six leaves per plant.

*Length.*—About 18.6 cm.

*Width.*—About 6.4 cm.

*Aspect.*—Upright to outwardly arching.

*Shape.*—Oblanceolate to narrowly oblong; slightly carinate.

*Apex.*—Unequal acute.

*Base.*—Sheathing. Sheath length: About 1.5 cm. Sheath width: About 1.3 cm. Sheath color: Close to 143A; strongly tinged towards the margins with close to 200A.

*Margin.*—Entire; slightly revolute.

*Texture and luster, upper and lower surfaces.*—Smooth, glabrous; slightly glossy.

*Venation pattern.*—Camptodromous.

*Color.*—Developing leaves, upper surface: Close to NN137A. Developing leaves, lower surface: Close to 146A; margin edges, tinged with close to 200A; fine speckles, close to NN137A. Fully expanded leaves, upper surface: Close to 147A overlain with close to 189A; margin edges, close to 147A; venation, close to 147A. Fully expanded leaves, lower surface: Close to 146A; margin edges, close to 147A; venation, close to 137A.

Inflorescence description:

*Appearance and flowering habit.*—Showy zygomorphic flowers arranged on axillary branched racemes; typically two inflorescences per plant; each inflorescence with about eight flowers; flowers face outwardly on arching inflorescences supported by upright peduncles; flowers with three petals, two lateral petals and one center petal transformed into a labellum and three sepals.

*Fragrance.*—None detected.

*Time to flower.*—Plants begin flowering about six months after planting; plants flower naturally during the winter into the spring.

*Flower longevity.*—Long flowering period, individual flowers maintain good substance for about eight weeks on the plant; flowers not persistent.

*Inflorescence length* (*lowermost flower to inflorescence apex*).—About 20.3 cm.

*Inflorescence width.*—About 14.3 cm.

*Flower buds.*—Height: About 2 cm. Diameter: About 1.5 cm by 1.7 cm. Shape: Broadly ovate. Color: Close to 152A to 152B; towards the apex and lower surface, tinged with close to 183B.

*Flower size.*—Large, about 8.7 cm (vertical) by 10 cm (horizontal).

*Flower depth.*—About 2.6 cm.

*Petals, quantity and arrangement.*—Three, two lateral petals and one center petal transformed into a labellum.

*Lateral petals.*—Length: About 4.8 cm. Width: About 6 cm. Shape: Reniform to lunate. Apex: Obtuse to broad and bluntly acute. Margin: Entire. Texture and luster, upper and lower surfaces: Smooth, glabrous, velvety; matte. Color: When opening, upper surface: Close to 72B; towards the margins and apex, close to N78A; at the base (at column connection), close to N78A. When opening, lower surface: Close to 77B; center, strongly tinged with close to 150C and 150D. Fully opened, upper surface: Close to N78B slightly blended with close to NN78B; at the base (at column connection), close to NN78A; at the margin edges, close to 76C to 76D; venation, darker than ground color, close to a blend of N78A and NN78A; color does not change with subsequent development. Fully opened, lower surface: Close to N75B; center, tinged with close to 157A; towards the margins, close to 77B and at the margin edges, close to 76C to 76D; venation, close to N75A; color does not change with subsequent development.

*Labella.*—Appearance: Three-parted with two lateral lobes and a central lobe. Length, lateral lobes: About 2 cm. Width, lateral lobes: About 1.7 cm. Length, central lobe: About 3.5 cm. Width, central lobe: About 7 mm to 24 mm. Shape, lateral lobes: Obovate. Shape, central lobe: Deltoid. Apex, lateral lobes: Rounded. Apex, central lobe: Cleft with two narrow and strongly recurved cirrose tips, about 1.5 cm in length and about 1 mm in width. Margins, lateral lobes: Entire; coarsely undulate. Margins, central lobe: Entire. Texture and luster, upper and lower surfaces: Smooth, glabrous, moderately velvety; matte. Callosities: Located at the base of the labellum and attachment point of the lateral petals; about 5 mm in length, about 7 mm in width and about 6 mm in height. Color: When opening, upper surface: Lateral lobes: Close to a blend of 185B and 187C; at the base, stripes, close to 157C; venation, close to a blend of 185A and 187B. Central lobe: Close to 187D; towards the margins and apex, close to 187C; at the base (at column connection), close to 157D with radial stripes, close to 175A; cirrose tips, close to 187C. Callosities: Close to 21C; fine dots, close to 185A. When opening, lower surface: Lateral lobes: Close to 197D; central blotch, close to 182C to 182D; apical margin, close to 70A and basal margin, close to 183B to 183C. Central lobe: Close to 183D; towards the apex, close to 156D and 157B; towards the base and at the base (at column connection), close to 156D; towards the margins, close to 185C and at the margin edges, close to 183B; cirrose tips, close to 187C. Fully opened, upper surface: Lateral lobes: Close to N78A; towards the base, close to a blend of 185B and 187C and at the base, stripes, close to 157C; venation, close to a blend of 185A and 187B. Central lobe: Close to 187D; towards the margins and apex, close to 187C; at the base (at column connection), close to 157D with radial stripes, close to 175A; main vein, close to 187C; cirrose tips, close to 187C. Callosities: Close to 21C; fine dots, close to 185A. Fully opened, lower surface: Lateral lobes: Close to 197D; central blotch, close to 182C to 182D; apical margin, close to 70A and basal margin, close to 183B to 183C. Central lobe: Close to 183D; towards the apex, close to 156D and 157B; towards the base and at the base (at column connection), close to 156D; towards the margins, close to 181B and at the margin edges, close to 181A; cirrose tips, close to 187C.

*Sepals.*—Quantity and arrangement: Three, one upper dorsal sepal and two lower lateral sepals. Length, dorsal sepal: About 4.8 cm. Width, dorsal sepal: About 3.4 cm. Length, lateral sepals: About 4.7 cm. Width, lateral sepals: About 3 cm. Shape, dorsal and lateral sepals: Ovate. Apex, dorsal sepal: Bluntly acute to occasionally, shallowly retuse. Apex, lateral sepals: Bluntly acute. Base, dorsal and lateral sepals: Truncate. Margin, dorsal and lateral sepals: Entire. Texture and luster, dorsal and lateral sepals, upper and lower surfaces: Smooth, glabrous, velvety; matte. Color, dorsal sepal: When opening, upper surface: Close to N79C; at the base (at column connection), close to N78A; venation, darker than N78A. When opening, lower surface: Close to a blend of 152D and 195A; towards the margins and apex, close to N77B; venation, close to 183B. Fully opened, upper surface: Close to N78A; towards the margins and apex, close to N78B; at the margin edges, close to 76C to 76D; at the base (at column connection), close to NN78A; venation, darker than a blend of N78A and NN78A. Fully opened, lower surface: Close to 196A to 196B; towards the margins and apex, close to N78D; venation, close to N77B. Color, lateral sepals: When opening, upper surface: Close to N79C; at the base, blotches and fine dots, close to 151D; venation, darker than N78A. When opening, lower surface: Close to a blend of 152D and 195A; towards the margins and apex, close to N77B;

venation, close to 183B. Fully opened, upper surface: Close to N78B; at the margin edges, close to 76C to 76D; at the base (at column connection), blotches and fine dots, close to 151D; venation, close to a blend of N78A and NN78A. Fully opened, lower surface: Close to 197D; towards the margins and apex, close to N78C to N78D; venation, close to N77B.

*Peduncles.*—Length: About 39.8 cm. Diameter: About 5 mm. Strength: Strong. Aspect: Upright to outwardly arching. Texture and luster: Smooth, glabrous; matte. Color: Close to 146A to 146B; densely covered with fine dots, close to between N186C and 200A.

*Pedicels.*—Length: About 3.5 cm. Diameter: About 4 mm. Strength: Moderately strong. Aspect: About 50° from peduncle axis. Texture and luster: Smooth, glabrous; matte. Color: Close to 148C; proximally, close 148A and distally, close to 156C.

*Reproductive organs.*—Androecium: Column length: About 9 mm. Column width: About 6 mm. Column color: Close to N78B; apical blotch, close to 76C. Pollinia quantity: Two. Pollinia diameter (per two pollinia): About 2.5 mm. Pollinia color: Close to 24A. Gynoecium: Stigma length: About 4 mm. Stigma width: About 5 mm. Stigma shape: Reniform. Stigma color: Close to 157D. Ovary length: About 8 mm. Ovary diameter: About 1 mm. Ovary color: Close to 144C. Seeds and fruits: To date, seed and fruit development have not been observed on plants of the new *Phalaenopsis.*

Pathogen & pest resistance: To date, plants of the new *Phalaenopsis* have not been shown to be resistant to pathogens and pests common to *Phalaenopsis* plants.

Temperature tolerance: Plants of the new *Phalaenopsis* have been observed to tolerate temperatures ranging from about 15° to about 40° C. and are suitable for USDA Hardiness Zones 10 to 12.

It is claimed:

1. A new and distinct *Phalaenopsis* plant named 'Gypsy Kiss' as illustrated and described.

* * * * *